(12) United States Patent
Friedli et al.

(10) Patent No.: US 11,628,249 B2
(45) Date of Patent: Apr. 18, 2023

(54) AMBULATORY INFUSION DEVICE

(71) Applicant: Roche Diabetes Care, Inc., Indianapolis, IN (US)

(72) Inventors: Kurt Friedli, Mannheim (DE); Michael Deppert, Bensheim (DE); Michael Lambertson, Mannheim (DE); Christian Würtele, Mannheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 116 days.

(21) Appl. No.: 16/258,141

(22) Filed: Jan. 25, 2019

(65) Prior Publication Data
US 2019/0167900 A1    Jun. 6, 2019

Related U.S. Application Data

(63) Continuation of application No. PCT/EP2017/069999, filed on Aug. 8, 2017.

(30) Foreign Application Priority Data

Aug. 9, 2016    (EP) .................................... 16183289

(51) Int. Cl.
*A61M 5/172*    (2006.01)
*A61M 5/142*    (2006.01)
(Continued)

(52) U.S. Cl.
CPC ............ *A61M 5/172* (2013.01); *A61M 5/142* (2013.01); *A61M 5/14244* (2013.01);
(Continued)

(58) Field of Classification Search
CPC .. A61M 5/172; A61M 5/142; A61M 5/14244; A61M 2005/3022; A61M 2209/02
See application file for complete search history.

(56) References Cited

U.S. PATENT DOCUMENTS 4,985,015 A  *  1/1991  Obermann ........ A61M 5/14216
                                                    604/152
5,328,460 A  *  7/1994  Lord ................. A61M 5/16854
                                                    128/DIG. 12
(Continued)

FOREIGN PATENT DOCUMENTS

EP    0 519 765 A1    12/1992
EP    2 163 273 A1    3/2010
(Continued)

OTHER PUBLICATIONS

International Search Report and Written Opinion, PCT/EP2017/069999, dated Oct. 17, 2017, 13 pages.

*Primary Examiner* — Amber R Stiles
*Assistant Examiner* — Leah J Swanson
(74) *Attorney, Agent, or Firm* — Bose McKinney & Evans LLP

(57) ABSTRACT

Disclosed is an ambulatory infusion device, including a control unit and an electroacoustic transducer. The control unit is configured to operate the electroacoustic transducer as noise emitter or to operate the electroacoustic transducer as noise receiver and to determine from a received noise that is received by the electroacoustic transducer a state of the ambulatory infusion device.

25 Claims, 3 Drawing Sheets

(51) Int. Cl.
*A61M 5/30* (2006.01)
*H04R 17/02* (2006.01)

(52) U.S. Cl.
CPC . *A61M 2005/3022* (2013.01); *A61M 2205/18* (2013.01); *A61M 2205/3317* (2013.01); *A61M 2205/3375* (2013.01); *A61M 2209/02* (2013.01); *H04R 17/02* (2013.01); *H04R 2400/01* (2013.01)

(56) References Cited

U.S. PATENT DOCUMENTS

| | | |
|---|---|---|
| 2002/0137478 A1 | 9/2002 | Masamura |
| 2005/0254344 A1* | 11/2005 | Barras ............... H04B 11/00 367/76 |
| 2006/0135907 A1* | 6/2006 | Remde ............. A61M 5/16831 604/67 |
| 2008/0125701 A1* | 5/2008 | Moberg ............. A61B 5/4866 604/67 |
| 2010/0264931 A1* | 10/2010 | Lindegger ............ G01R 31/40 324/511 |
| 2011/0054334 A1 | 3/2011 | Fischell et al. |
| 2011/0163880 A1 | 7/2011 | Halff et al. |
| 2012/0209183 A1 | 8/2012 | Gray |
| 2012/0296224 A1 | 11/2012 | Klee et al. |
| 2014/0262252 A1 | 9/2014 | Slepicka et al. |
| 2015/0025499 A1 | 1/2015 | Trock et al. |
| 2015/0073345 A1 | 3/2015 | Matsuzaki et al. |

FOREIGN PATENT DOCUMENTS

| | | | |
|---|---|---|---|
| EP | 2 422 830 A1 | | 2/2012 |
| EP | 2 799 098 A1 | | 11/2014 |
| EP | 2 881 128 A1 | | 6/2015 |
| JP | 2015-505258 A | | 2/2015 |
| JP | 2015-054015 A | | 3/2015 |
| JP | 2016-518157 A | | 6/2016 |
| RU | 2 578 810 C2 | | 3/2016 |
| WO | WO 2004/110528 A1 | | 12/2004 |
| WO | WO 2010/026580 A2 | | 3/2010 |
| WO | WO 2013/096713 A2 | | 6/2013 |
| WO | WO-2015046396 A1 * | 4/2015 | ......... A61M 5/1452 |
| WO | WO 2015/187793 A1 | | 12/2015 |
| WO | WO 2015/046396 A1 | | 3/2017 |

* cited by examiner

AMBULATORY INFUSION DEVICE

RELATED APPLICATIONS

This application is a continuation of PCT/EP2017/069999, filed on Aug. 8, 2017, which claims priority to EP 16 183 289.4, filed on Aug. 9, 2016, the entire disclosures of both of which are hereby incorporated herein by reference.

BACKGROUND

The present disclosure lies in the field of ambulatory infusion devices that include an electroacoustic transducer, and to methods for operating an electroacoustic transducer of an ambulatory infusion device. Ambulatory infusion devices are commonly used in a number of therapies, in particular the treatment of Diabetes Mellitus via Continuous Subcutaneous Insulin Infusion (CSII).

Ambulatory infusion devices are known in the therapy of Diabetes Mellitus and a number of further therapies that involve substantially continuous drug infusion, such as certain pain therapies or cancer therapies, for many years. Modern ambulatory infusion devices are miniaturized computerized devices that are typically sized to fit, e.g., in a trousers' pocket and/or are designed to be attached directly and typically adhesively to the user's body. The devices are carried substantially continuously night and day and are designed to administer drug substantially continuously according to a typically time-variable basal schedule as well as drug boli of desired amount on demand.

Because insulin formulations that are infused in CSII and other typical drugs that may be infused are highly critical and require precise dosing, safety and the detection of hazardous situations (e.g., fluidic blockages, empty drug reservoirs, or leakages) and of device defects are of high importance. Therefore, state of the art ambulatory infusion devices typically include a number of sensors as well as safety circuitry and software/firmware routines for monitoring correct operation and carrying out testing or checking routines. Further, ambulatory infusion devices typically include an acoustic indicator, e.g., a buzzer, and often also a tactile indicator, e.g., a pager vibrator, for providing general user feedback and in particular for providing alarms or alerts in situations that require the user's attention.

However, since a small size and weight are of high and increasing importance for comfort and discretion reasons, the space that is available for sensors and safety circuitry is strictly limited. Given the generally typical high therapy costs, the device costs are a further point of concern and the number of components should accordingly be small.

WO 2004/110528 A1 discloses using a microphone for detecting various device defectives and/or hazardous situations, including manual or automated noise analysis.

EP 0 519 765 discloses the use of a piezo sensor for picking up an acoustic signal that is generated by an implantable infusion pump and evaluating the signal for fault detection purposes.

U.S. Pat. No. 4,985,015 discloses an implantable infusion device with a piston pump where a characteristic noise that is generated by piston pump during operation is used for monitoring and controlling the infusion device.

EP 0 519 756 discloses using a stethoscope for determining operation of an implantable infusion device.

SUMMARY

Based on this background, the present disclosure improves the state of the art regarding ambulatory infusion devices in particular with respect to an efficient component use. Particular further advantages of specific embodiments are described further below as the description proceeds. This disclosure is based on the insight that an electroacoustic transducer that is generally present in an ambulatory infusion device as acoustic indicator may be favorably additionally used for picking up acoustic signals that are generated by the ambulatory infusion devices during regular operation and/or under certain circumstances.

In an aspect, an ambulatory infusion device is disclosed, including a control unit and an electroacoustic transducer. The control unit is configured to operate the electroacoustic transducer as noise emitter. The control unit is further configured to operate the electroacoustic transducer as noise receiver and to determine from a received noise that is received by the electroacoustic transducer a state of the ambulatory infusion device. The operation of the transducer as noise emitter and noise receiver are typically alternatives and the transducer operates as either noise emitter or alternatively as noise receiver. It is, however, also possible to operate the transducer and/or a further transducer as described further below as noise emitter and noise receiver simultaneously.

The determination may include qualitative aspects such as the general shape of the frequency spectrum, as well as quantitative aspects such as amplitude and/or power of the received signal, the amplitude of particular spectral components, or the like.

In such a device, an electroacoustic transducer serves a dual purpose. When operated as noise emitter, the electroacoustic transducer serves as acoustic indicator (loudspeaker, buzzer) for providing acoustic indications and in particular acoustic alarms to the device user. When operated as noise receiver, the transducer serves as microphones that pick up a received noise that is subsequently evaluated. Various particular examples of noise and evaluation routines are discussed further below. As explained further below, operating the transducer as noise receiver is particularly favorable in the context of testing or verifying correct operation of the ambulatory infusion device or its components, respectively.

The ambulatory infusion device is an extracorporeal device and may especially be a device as used in the diabetes therapy by CSII as explained before and as generally known in the art.

In this document, the expression "noise" refers to an acoustic signal with acoustic waves, typically at least partly in the audible spectrum. Generally, the expressions acoustic signal, noise and sound are understood as synonyms. The noise may be an intentionally generated noise or sound signal, such as alarm signals, that are generated for providing user feedback, alarms and the like. However, it may also be operational noise that inevitably results from operation of the ambulatory infusion device or its components, such as drive noise.

A sound signal that is generated for providing user feedback or alarming favorably has a well-defined sound pattern and may, e.g., be a sound of constant and known frequency, a sound pattern of alternating frequencies, a sound pattern of increasing and/or decreasing amplitude, or the like.

In an embodiment, the ambulatory infusion device may include a further electroacoustic transducer, distinct from the electroacoustic transducer. The control unit may here be configured to operate the further electroacoustic transducer as further noise emitter. Such further electroacoustic transducer is in particular favorable for redundancy purposes and/or for providing acoustic alarms with increased sound level as explained further below.

In an embodiment with a further electroacoustic transducer, the control unit may be configured, while operating the further electroacoustic transducer as noise emitter to emit a further emitted noise, to simultaneously operate the electroacoustic transducer as noise receiver. Determining from the received noise a state of the ambulatory infusion device includes for this type of embodiment determining whether the received noise corresponds to the further emitted noise.

In such embodiment, correct operation of the further transducer—operating as buzzer or loudspeaker—is checked using the transducer as microphone. In case no noise is received or the received noise does not correspond to the further emitted noise as expected, a warning or alarm is favorably provided.

Checking correct operation of a buzzer or loudspeaker by picking up and evaluating the emitted nose signal is favorable over a pure electrical testing because it considers all aspects, and in particular potential problems or defects, that are not apparent from a pure electrical testing or checking, such as, e.g., dirt that negatively affects the noise emission or a broken fixing of the transducer. In typical devices according to the state of the art, in contrast, an electroacoustic transducer (buzzer or loudspeaker) is only checked electrically, using technics such as electric impedance measurement.

In addition, deviations between the noise that shall be emitted and the received noise may be indicative of further device defects, such as a broken housing that results in the transducer being detuned.

Determining whether the received noise corresponds to the emitted noise favorably includes evaluating the frequency and/or amplitude of the received noise. The received noise that is expected for correct operation is determined by the sound pattern, in particular amplitude and/or frequency pattern of the sound pattern of the emitted noise.

In an embodiment with a transducer and a further transducer, the transducer and the further transducer are favorably arranged in structure-borne and/or airborne acoustic coupling, such that noise that is emitted by the further transducer is received by the transducer and/or noise that is emitted by the transducer is received by the further transducer. Generally, good acoustic coupling is favorable. For this purpose, the transducer and the further transducer may be arranged, e.g., next to each other in close proximity and side-by-side.

In many cases, a transducer that is present in a portable device such as an ambulatory infusion device as buzzer/loudspeaker is realized as a disk-shaped piezoelectric transducer. In a particularly favorable embodiment with a disk-shaped transducer and a further disc-shaped transducer, the transducer and the further transducer are arranged as a stack and are favorably aligned with each other. Typically, both disk-shaped transducers are of identical design. The resulting stack has substantially the footprint of a single transducer and double the height of a single transducer. Favorably, the transducer and the further transducer are mechanically and acoustically coupled by adhesive bonding.

In an embodiment with a further electroacoustic transducer, the control unit may be configured to control the further electroacoustic transducer to operate as further noise receiver and to determine from a further received noise that is received by the further electroacoustic transducer a further state of the ambulatory infusion device. Favorably in such embodiment, the control unit is further configured, while operating the further electroacoustic transducer as noise receiver, to operate the electroacoustic transducer as noise emitter to emit a noise signal. Determining the further state of the ambulatory infusion device may here include determining whether the further received noise corresponds to an emitted noise that is emitted by the electroacoustic transducer.

For such embodiment, correct operation of the electroacoustic transducer as buzzer or loudspeaker may be acoustically checked using the further electroacoustic transducer as microphone in an analogue way to the above-described embodiment.

In an embodiment with a further electroacoustic transducer, the control unit may be configured to simultaneously operate both the electroacoustic transducer and the further electroacoustic transducer as acoustic noise emitters. Here, the control unit may further be configured to actuate both the electroacoustic transducer and the further electroacoustic transducer in common, in particular synchronously. This type of embodiment allows providing acoustic indications and in particular alarms with a higher sound level as compared to a single buzzer or loudspeaker. This is particularly favorable because the sound level of alarms is a generally critical issue in particular for water-protected or watertight devices—as typically the case for ambulatory infusion device—since buzzers or loudspeakers as noise emitting elements need to be arranged inside the cases, resulting in non-ideal noise emission conditions.

In an embodiment, the control unit may be configured to control a drug administration, the ambulatory infusion device thereby emitting an operational noise. Here, determining the operational state of the ambulatory infusion device may include evaluating the operational noise. The operational noise is a noise that is emitted by a drive (motors, gears, bearings, threaded spindles, etc.) and is characteristic for the ambulatory infusion device in dependence of its design. Evaluating the operational noise may include technics and algorithms as generally known in the art for evaluating acoustic signals, such as filtering (e.g., high pass, low pass and band pass filtering), averaging, Fast Fourier Transformation (FFT), peak detection, pattern recognition and the like. Signal condition and evaluation may be done via hardware and/or software respectively firmware that runs on microcomputer or microcontrollers of the control unit in any desired combination.

In an embodiment that includes evaluating an operational noise, the evaluation may include determining whether the drive noise corresponds to an expected operational noise. Favorably the ambulatory infusion device is configured to generate a warning/and or an alarm if the received noise does not correspond to respectively match the expected operational noise.

In an embodiment that includes evaluating an operational noise, the evaluation may include determining whether the operational noise is indicative for a defect.

In an embodiment that includes evaluating an operational noise, the ambulatory infusion device includes an electric drive and the operational noise may include a drive noise that is emitted by the electric drive.

Evaluating the operational noise may include evaluating the operation time of the drive as reflected by the drive noise during drug administration, and comparing the determined operation time with an expected operation time in accordance with a drug amount that is administered. In this way, erroneous underdoing that may result from a defect may be determined. Further, defects that are associated with the drive operating unintentionally continuously may be detected. Such defects are particularly critical as they result in an uncontrolled administration of a large drug amount, potentially the whole reservoir content.

Evaluation of the operational noise may include detecting an unexpected interruption in the operational noise, in particular drive noise, during operation of the drive. In this way, loose contacts can be favorably detected.

Evaluation of the operational noise may further include determining from the operational noise, in particular drive noise, a rotational direction of the drive. The rotational direction can be determined based on differences in the emitted drive noise.

Evaluation of the operational noise may include detecting the occurrence of step losses if the drive includes a stepper motor or brushless DC motor. Step losses may result from a mechanical overload or be indicative of a device defect.

Evaluation of the operational noise, in particular drive noise, may include evaluating a relation between the operational noise and a further sensor signal, the further sensor signal being generated by a drive sensor, and determining whether the relation matches an expected relation. The drive sensor may in particular be an encoder, such as an optical and/or magnetic rotational encoder that is coupled to a drive shaft and used for supervising and/or control of the drive. If the ambulatory infusion device operates correctly, the operational noise and the further sensor signal match.

In an embodiment that includes evaluating an operational noise, the evaluation may include determining whether the operational noise is indicative for a fluidic blockage of an infusion path.

In an embodiment that includes evaluating an operational noise, the operational noise includes a valve switching noise.

In an embodiment, determining the operational state of the ambulatory infusion device includes detecting the occurrence of a mechanical shock.

In an embodiment, the method includes recording a received noise and/or further received noise in a memory of the ambulatory infusion device and/or an external device. The recorded signals may be used for fault analysis purposes. Further, the control unit may be configured to compare the received noise and/or further received noise with previously recorded noise as stored in the memory. In this way, long-term changes in the operational sound, in particular drive noise, as indicative, e.g., of excessive wear, may be detected.

In an embodiment, the ambulatory infusion device includes a drive that is designed to generate, in operation, at least one dedicated characteristic noise signal, e.g., click noise, that is associated with correct operation of the drive. Evaluating the received noise and/or further received noise signal may include determining the presence of the dedicated characteristic noise signal. Favorably, an alarm is provided if the dedicated characteristic noise is not detected.

In an embodiment, the ambulatory infusion device includes a tactile indicator, such as a pager vibrator. The control unit may be configured to activate the tactile indicator and to simultaneously operate the electroacoustic transducer as noise receiver, wherein determining from the received noise a state of the ambulatory infusion device includes determining whether the received noise corresponds to a noise that is expected to be received as result of the operating tactile indicator. For this type of embodiment, correct operation of a tactile indicator may be checked in the same way as the electroacoustic transducer and/or a further electroacoustic transducer. This type of embodiment relies on the fact that typical tactile indicators, in particular pager vibrators, also emit noise that may be received by an electroacoustic transducer that is operating as microphone.

In a further aspect, an ambulatory infusion system is disclosed. The ambulatory infusion system includes an ambulatory infusion device and a remote device. The ambulatory infusion device includes a control unit and an electroacoustic noise emitter, such as a buzzer or loudspeaker that is operable under control of the control unit. The remote device is favorably a handheld device such as a diabetes management device that may optionally also include a blood glucose meter, a remote control device, or a general purpose device, e.g., a smart phone. The remote device includes a noise receiver, e.g., a microphone. The ambulatory infusion device and the remote device are configured to operatively couple via a wireless communication link, typically an RF communication link, that may, e.g., be based on the Bluetooth standard or operate according to a proprietary standard. The control unit of the ambulatory infusion device is configured to activate the noise emitter to emit a noise, and to further transmit a corresponding noise emission notification via the communication link to the remote device. The remote device is configured to activate, upon reception of the noise emission notification, the electroacoustic receiver and is further configured to determine whether a received noise that is received by the noise receiver corresponds to an expected emitted noise that is expected to be emitted by the noise emitter. Favorably, the remote device is further configured to provide an alarm if the received noise does not correspond to the expected emitted noise.

The noise emitter of the ambulatory infusion device may be a dedicated noise emitter (buzzer, loudspeaker) or be an electroacoustic transducer that is also operable as nose receiver. Similarly, the noise receiver of the remote device may be a dedicated noise receiver (microphone) or may be an electroacoustic transducer that is also operable as noise emitter.

For this type of ambulatory infusion system, the noise emitter of the ambulatory infusion device can be acoustically checked in substantially the same way and applying the same methods as discussed before and/or further below in the context of exemplary embodiments. The emitted noise, however, is received by a noise receiver of the remote device.

In a further aspect, disclosed is a method for operating an electroacoustic transducer that is part of an ambulatory infusion device. The method includes operating the electroacoustic transducer as noise emitter to emit an emitted noise. The method further includes operating the electroacoustic transducer as a noise receiver and determining a functional state of the ambulatory infusion device from a received noise that is received by the electroacoustic transducer. The operation as noise emitter and noise transducer are typically alternatives and the transducer may at a given point in time, be operated as noise emitter or noise receiver. In some embodiments, however, a transducer may be operated as noise emitter and noise receiver simultaneously.

In an embodiment, the method may include operating a further electroacoustic transducer, distinct from the electroacoustic transducer, as noise emitter and simultaneously operating the electroacoustic transducer as noise receiver. Here, determining from the received noise a state of the ambulatory infusion device may include determining whether the received noise corresponds to a further emitted noise that is emitted by the further electroacoustic transducer.

In an embodiment, the method may include simultaneously operating both the electroacoustic transducer and the further electroacoustic transducer as acoustic noise emitters. Here, the method may further include actuating both the electroacoustic transducer and the further electroacoustic transducer in common, in particular synchronously.

Further aspects and particular embodiments of ambulatory infusion devices as well as methods are discussed further below in the context of exemplary embodiments.

In a further aspect, disclosed is a method for supervising operation and/or monitoring an ambulatory infusion device. The method may include operating an electroacoustic transducer as explained before and/or further below. The method may further include providing an alert in case the determined operational state is indicative for a defect and/or malfunction and/or hazardous situation.

Embodiments of an ambulatory infusion device in accordance with the present disclosure may in particular be designed to carry out a corresponding embodiment of a method in accordance with the present disclosure. Likewise, methods in accordance with the present disclosure may in particular be carried out with and/or by an ambulatory infusion device in accordance with the present disclosure. The disclosure of particular embodiments of a method therefore discloses the same time corresponding embodiments of an ambulatory infusion device. Likewise, the disclosure of particular embodiments of an ambulatory infusion device discloses at the same time an embodiment of a corresponding method.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
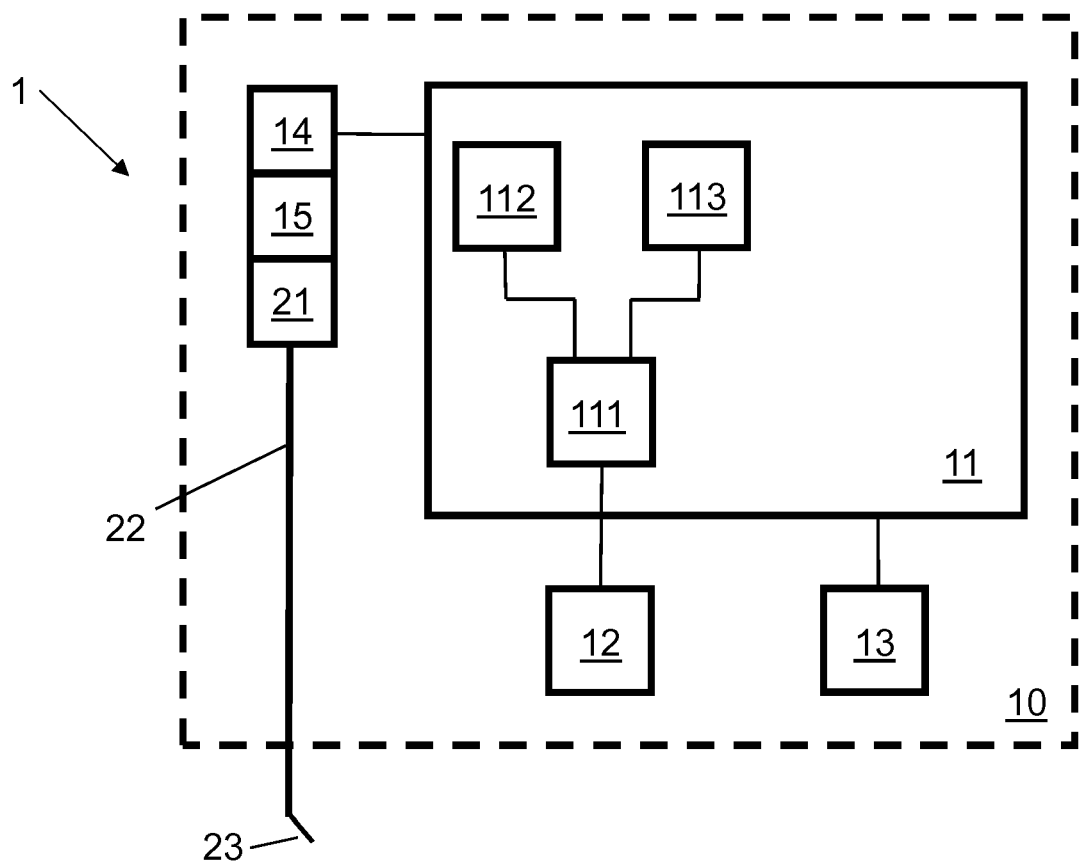
FIG. 1 shows an exemplary embodiment of an ambulatory infusion device.

In the following, reference is first made to FIG. 1. FIG. 1 shows an exemplary embodiment of an ambulatory infusion device 1 in accordance with the present disclosure in a schematic view.

The ambulatory infusion device 1 includes a control unit (also referred to as "controller") 11 that is realized by electronic circuitry, typically including one or more microcomputer(s) or microcontroller(s) as well as supplementary circuitry as generally known in the art. The ambulatory infusion device 1 further includes an electric drive that is typically based on a motor 14, e.g., a DC motor, a stepper motor or a brushless DC motor as generally known in the art. The motor 14 is operatively coupled with a spindle drive unit (also referred to as "drive") 15. The motor 14 and the spindle drive unit 15 form, in combination, a drive chain of the ambulatory infusion device 1. In an operational configuration, the spindle drive unit 15 is operatively coupled with the piston of a liquid drug cartridge 21. By displacing the piston of the cartridge 21 in a controlled way, drug is expelled out of the cartridge 21 via infusion tubing 22 and infusion cannula 23 under control of the control unit 11. The ambulatory infusion device 1 further includes an electroacoustic transducer 12 in operative coupling with the control unit 11. Further, the ambulatory infusion device 1 includes a tactile indicator that is realized as a pager vibrator 13 in operative coupling with and controlled by the control unit 11.

To this extent, the ambulatory infusion device 1 provides typical functionality of ambulatory infusion devices as used, for example, in diabetes therapy. In particular, the ambulatory infusion device 1 is designed for administering liquid drug, for example in a liquid insulin formulation, according to a time-varying basal schedule substantially continuously night and day, and for additionally administering drug boli of desired size on demand. It is noted that the ambulatory infusion device 1 may include further components such as a power supply, an input unit for inputting user commands, a display, one or more communication interfaces, an optical and/or rotational encoder as part of or in operative coupling with the motor 14, and a force sensor that measures a force that is exerted by the drive chain onto the piston. Corresponding components and arrangements are generally known in the art.

The ambulatory infusion device 1 further includes a housing 10 that encloses its components, typically including the cartridge 21, in an operational state.

The control unit 11 controls the overall operation of the ambulatory infusion device 1, including the motor 14 for drug administration as explained before. The control unit 11 further controls the operation of the transducer 12 and associated components as discussed in following.

For controlling operation of the transducer 12, the control unit 11 includes a switching module 111, a noise generator module 112 and an evaluation module 113. It is noted that the separation of functional modules as shown in FIG. 1 and following figures is generally exemplary and made to aid the reader's understanding. In a practical embodiment of the ambulatory infusion device 1 and in particular of the control unit 11, a number of functional modules may be realized fully or partly integral with each other and may further be realized by hardware and/or software/firmware in any desired combination.

The transducer 12 is exemplarily realized as piezoelectric transducer but may alternatively be of different design and realized, e.g., as electrodynamics transducer. The transducer 12 is operable as both noise emitter (loudspeaker, buzzer) or as noise receiver (microphone).

For operating as noise emitter, the switching module 111 operatively connects the transducer 12 with noise generator module 112 as power driver circuit. When operating as noise emitter, the transducer 12 serves as acoustic indicator for the purpose of providing acoustic user feedback, and/or alerting the user of situations that require particular attention and/or actions, such as defects of the ambulatory infusion device 1, a blocked infusion tubing 22 and/or infusion cannula 23 (occlusion), an empty cartridge 21, or the like. The pager vibrator 13 is used in the same way as the acoustic transducer 12 in addition and/or alternatively. Favorably, either or both of the electroacoustic transducer 12 and/or the pager vibrator 13 may be used for providing uncritical indications and/or user feedback, while both the electroacoustic transducer 12 and the pager vibrator 13 are activated by the control unit 11 in case of a critical situation that requires user's immediate attention.

For operating as noise receiver, the switching module 111 operatively connects the electroacoustic transducer 12 with the evaluation module 113, where a signal that is received via the electroacoustic transducer may be processed and/or conditioned as required, e.g., filtered, amplified and/or converted from analogue to digital, and is evaluated.

When operating as noise receiver, the electroacoustic transducer 12 serves for receiving an operational noise of the ambulatory infusion device 1 as received noise that is transformed and further processed respectively evaluated by the evaluation module 113. The electroacoustic transducer is acoustic coupled with the drive chain (in particular motor 14 and spindle drive unit 15), and with the pager vibrator 13 via structure-borne and/or airborne acoustic coupling.

The control unit 11 may in particular operate the electroacoustic transducer 12 as noise receiver during drug administration, i.e., simultaneously to activating the motor 14 for a basal drug administration or a drug bolus administration. In operation, the motor 14 emits a drive noise that is generally characteristic for the design of the motor 14 as well as its operational conditions (in particular rotational speed, load). Similarly, the spindle drive unit 15 emits in operation a noise in dependence of its design and operational conditions. In combination, the noise that is emitted by the spindle drive unit 15 and the motor 14 is an operational noise during drug administration. The evaluation module 113 is configured to evaluate the operational noise that is received by the electroacoustic transducer 12 while the motor 14 is active and to determine whether the operational noise corresponds to an expected operational noise.

For this purpose, the evaluation module 113 may evaluate the received noise in the time domain and/or in the frequency domain (based, e.g., on Fast Fourier Transformation, FFT), and/or evaluate characteristics such as an overall signal amplitude, effective value (Root Mean Square, RMS), and the like. Evaluation of the received noise is typically implemented by way of software respectively firmware code, but may also include dedicated hardware components in addition or alternatively.

Typical device defects, in particular defects of the drive chain, result in a deviation from the expected operational noise and may therefore be detected by the evaluation module 113. For example, excessive wear (beyond a usual and accepted level), dirt or stain typically results in an increased overall noise level. A broken or defective tooth of a reduction gear that typically forms part of the motor 14 and/or the spindle drive unit 15 results in a characteristic signal with a frequency dependent on the rotational speed. Further defects that may be detected are explained above in the context of the general description.

In addition to determining whether the operational noise corresponds to an expected operational noise during drug administration, the control unit 11 may activate the motor 14 and determine whether the operational noise corresponds to the expected operational noise as part of a drive testing routine. Such drive testing routine may favorably be carried out automatically, e.g., when replacing the drug cartridge 21. In case of the spindle drive unit 15 being an integral part of the ambulatory infusion device 1 and accordingly needing to be moved from an advanced position (corresponding to an empty drug cartridge 21) to a retracted position (corresponding to a full drug cartridge 21), a drive testing routine may be carried out while activating the motor 14 for the retraction movement.

During drug administration, determining whether the received noise corresponds to an expected operational noise is favorably further used for determining whether the operational noise is indicative of a blockage (occlusion) of the fluidic path, in particular the infusion tubing 22 and/or the infusion cannula 23. In case of an occlusion, any attempt to administer further drug from the cartridge 21 (more particular, activation of the motor 14) results in a steep increase of the internal fluidic pressure and accordingly a steep increase of the force against which the drive chain acts, until the motor 14 finally stalls. This process is typically accompanied by a characteristic changes in the motor noise over time, typically in particular a temporary increase of the overall operational noise before the motor 14 finally stalls.

As mentioned before, the electroacoustic transducer 12 is favorably further in acoustic coupling with the pager vibrator 13 and the evaluation unit 113 may be configured to determine whether a received noise that is received by the electroacoustic transducer 12 while simultaneously activating the pager vibrator 13 corresponds to an expected noise. The expect noise depends on the design and control of the pager vibrator 13 and is—for a typical design with a miniaturized motor and an eccentric mass that is coupled to its drive shaft—dependent on the rotational speed. Actuating the pager vibrator 13 and determining whether the electroacoustic transducer 12 receives a corresponding signal may be carried out as part of a dedicated pager testing routine under control of the control unit 11. Such pager testing routine may be initiated, e.g., when powering up the ambulatory infusion device 1, when replacing the drug cartridge 21, and/or with a pre-determined time interval, e.g., once a day. A pager testing routine may also be carried out when activating the pager vibrator 13 for providing indications to the device user.

A number of further methods, routines and algorithms for evaluating a signal that is received by an electroacoustic transducer or microphone for determining an operational state of an ambulatory infusion device are disclosed in WO 2004/110528 A1 to which reference is made in this regard.

Figure 2:
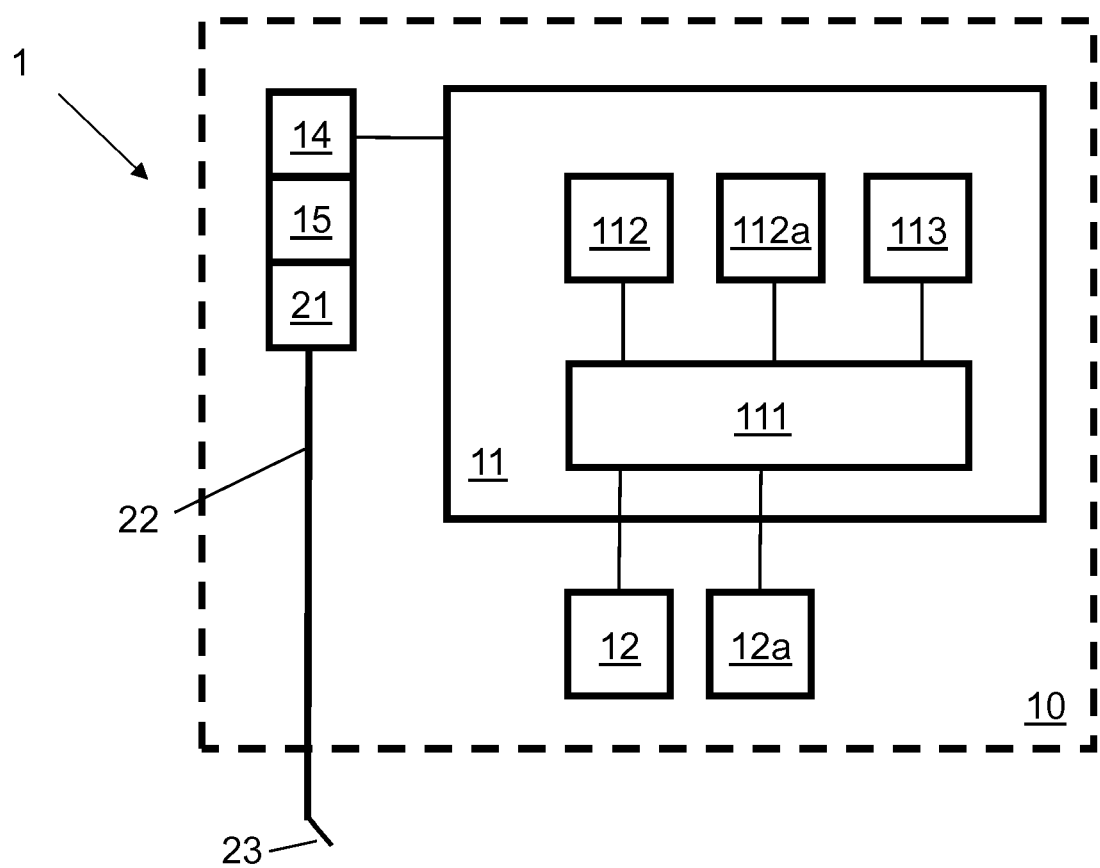
FIG. 2 shows a further exemplary embodiment of an ambulatory infusion device.

In the following, reference is additionally made to FIG. 2, illustrating a further embodiment of an ambulatory infusion device 1 in accordance with the present disclosure. Since the embodiment of FIG. 2 corresponds to the embodiment of FIG. 1 in a number of aspects, only differences are discussed in the following.

In the embodiment of FIG. 2, a further electroacoustic transducer 12a is present in addition to the electroacoustic transducer 12, and a further noise generator module 112a is provided in addition the noise generator module 112. The noise generator module 112 is associated with the transducer 12 and the further nose generator module 112a is associated with the further transducer 12a. The transducer 12 and the further transducer 12a may be of identical design, e.g., piezoelectric buzzers, but are distinct and operable independent from each other. Both the transducer 12 and the further transducer 12a may be operated as sound emitter or as sound receiver. The switching module 111 is configured to simultaneously operatively couple the transducer 12 with the noise generator module 112 and the further transducer 12a with the further noise generator module 112a to operate both the transducer 12 and the further transducer 12a as sound emitters. The switching module 111 is further configured to operatively couple either of the transducer 12 or the further transducer 12a with its associated sound generator module 1112, 112a for operation as noise emitter, and to simultaneously operatively couple the other of the transducer 12 and the further transducer 12a with the evaluation module 113 for operation as noise receiver.

The transducer 12 and the further transducer 12a are functionally distinct from each other and may be operated separate from each other. They are, however, in acoustic coupling such that an emitted noise that is emitted by the transducer 12 may be received by the further transducer 12a as further received noise. Similarly, a further emitted noise that is emitted by the further transducer 12a may be received by the transducer 12 as received noise. In a typical exemplary embodiment, the transducer 12 and the further transducer 12a are piezoelectric transducers of-disk-like shape that are stacked on top of each other and coupled via adhesive bonding as described above.

For providing acoustic indications to the device user, either or both of the transducer 12 and the further transducer 12a may be operated as noise emitter respectively acoustic indicator. In an embodiment, the control unit 11 controls activation of both transducers to be generally activated in common, resulting in an increased sound level as compared to a single transducer, with the noise generator module 112 and the further noise generator module 112a generating, e.g., identical noise signals. Alternatively, the control unit controls the activation of only one of the transducer, e.g., transducer 12, when providing uncritical user feedback and/or general information, but controls the activation of both the transducer 12 and the further transducer 12a for providing alarms that require direct attention, e.g., a device error or an occlusion as explained before. Using both transducers in such situations is favorable since the acoustic alarm level is a critical issue, in particular in case of a hermetically sealed respectively water tight housing 10, and a sufficient acoustic alarm level, in particular a pre-defined minimum alarm level, is typically further to be met for regulatory reasons.

For testing correct operation, one of the transducer 12 and the further transducer 12a is operated as noise emitter, while the other of the transducer 12 and the further transducer 12a is operated as noise receiver and it is determined whether the noise that is received by the receiving transducer corresponds to an expected noise as emitted by the emitting transducer. A corresponding testing routine may carried out as dedicated transducer testing routine in the same way as a before-described pager testing routine. Such transducer testing routine may be initiated, e.g., when powering up the ambulatory infusion device 1, when replacing the drug cartridge 21, and/or with a pre-determined time interval, e.g., once a day. A transducer testing routine may also be carried out when activating the transducer 12 and/or the further transducer 12a for providing indications or alarms to the device user.

Figure 3:
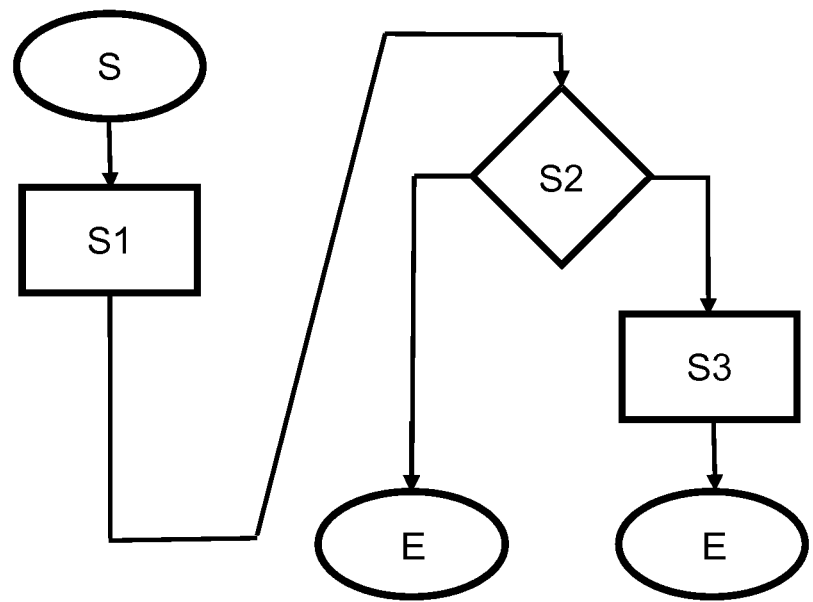
FIG. 3 illustrates an operational flow of a transducer testing routine.

In the following, reference is additionally made to FIG. 3, schematically illustrating the operational flow for an embodiment of a transducer testing routine that may be carried out with an ambulatory infusion device 1 as shown in FIG. 2.

The testing routine is initiated in step (S). In subsequent step (S1) the switching module 111 operatively couples the transducer 12 with the noise generator module 112 for operation as noise emitter and operatively couples the further transducer 12a with the evaluation module 113 for operation as noise receiver. Further in step (S1), the transducer is 12 is activated as noise emitter and emits a noise signal that is generated by the noise generator module 112, while the further transducer 12a is operated as noise receiver, with the received noise being evaluated by the evaluation unit 113. In subsequent step (S2), it is determined whether the noise as received by the further transducer 12a corresponds to the noise signal as generated by the noise generator module 112 respectively as emitted by the transducer 12 and the operational flow branches in dependence of the result. In the affirmative case, the test is successful and ends in step (E). In the opposite case, step (S3) is carried out where a corresponding warning or alarm is generated and displayed, e.g., on a display of the ambulatory infusion device and/or transmitted to a further device, e.g., a handheld device, smart phone or the like and the transducer testing routine ends (E). Further in step S3, the further acoustic transducer 12a (i.e., the transducer that has not been activated to operate as noise emitter in step S2) may alternatively or additionally be operatively coupled with the noise generator module 112 and subsequently controlled to emit an acoustic warning or error signal. In this way, an acoustic alarm may be provided event though transducer 12 is defective. It is noted that the procedure of FIG. 3 may also be carried out in an analogue way with the role of the transducer 12 and the further transducer 12a being reversed.

Figure 4:
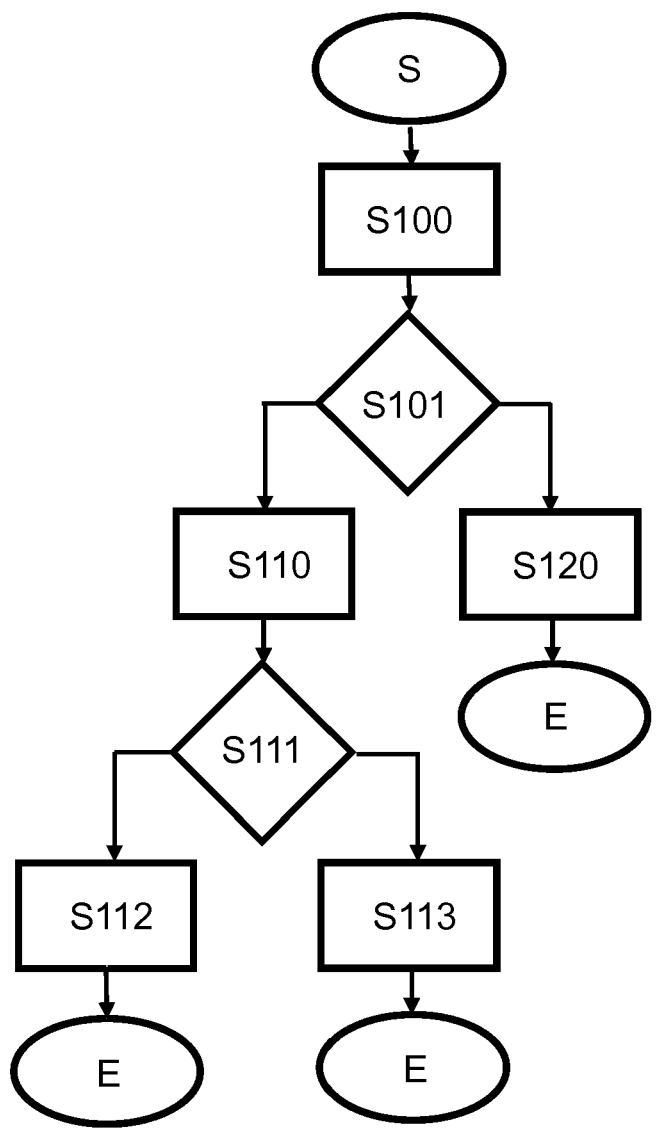
FIG. 4 illustrates an operational flow for an alarming routine.

In the following, reference is additionally made to FIG. 4, illustrating an exemplary operational flow for an alarming routine that provides an acoustic alarm for the user of ambulatory infusion device 1 according to FIG. 2. The operational flow includes a testing routine for the transducer 12 and the further transducer 12a.

The alarming routine is initiated in step (S). In subsequent step (S100), the switching module 111 operatively couples the transducer 12 with the noise generator module 112 for operation as noise emitter and operatively couples the further transducer 12a with the evaluation module 113 for operation as noise receiver. Further in step (S100), the transducer is 12 is activated as noise emitter, thus emitting an acoustic alarm signal, while the further transducer 12a is operated as noise receiver, with the received noise being evaluated by the evaluation unit 113. In subsequent step (S101), it is determined whether the noise as received by the further transducer 12a corresponds to the alarm signal as generated by the noise generator module 112 respectively as emitted by the transducer 12, and the operational flow branches in dependence of the result.

If the result is affirmative in Step S101, steps S110, S111 are subsequently carried out that generally correspond to steps S100, S101 as discussed before. The role of the transducer 12 and the further transducer 12a, however, is reversed. That is, the further transducer 12a is operatively coupled with the further noise generator module 112a for operation as noise emitter and the transducer 12 is operatively coupled with the evaluation module 113 for operation as noise receiver.

If the result is affirmative in step S111, both the transducer 12 and the further transducer operate correctly. In subsequent step (S112), the switching module 111 operatively couples the transducer 12 with the noise generator module 112 and simultaneously operatively couples the further transducer 12a with the further noise generator module 112a, and both the transducer 12 and the further transducer 12a are operated as noise emitters for providing an acoustic alarm.

If the signal that is received by the further transducer 12a (step (S100)) respectively the signal that is received by the transducer 12 (step (S110)) does not correspond to the signal that is generated by the noise generator module 112 respectively the further noise generator module 112a, the operational flow branches to step (S120) in step (S101) respectively to step (S113) in step (S111). In step (S120), the alarm signal is emitted by the further transducer 12a, and in step (S113) the alarm signal is emitted by the transducer 12. In both step (S120) and (S113), a corresponding warning or alarm is generated and displayed, e.g., on a display of the ambulatory infusion device and/or transmitted to a further device as explained before, providing a warning that the transducer 12 respectively the further transducer 12a is defective.

The ambulatory infusion devices as shown in FIG. 1, FIG. 2 and the operational flows as illustrated in FIG. 3, 4 may be modify and varied in a number of ways.

In the embodiment of FIG. 2, separate noise generator modules 112, 112a are foreseen that are separately associated with the transducer 12 and the further transducer 12a. This is advantageous in so far as the redundancy that is provided by the two transducers 12, 12a is extended to the noise generator modules 112, 112a. If, for example, the noise generator module 112 (including the power or driver circuitry) is defective, acoustic alarms may still be provided via the further noise generator module 112a and the further transducer 12a. Alternatively, however, the further noise generator module 112a may be omitted and the noise generator module 112 may be operatively coupled with either or both of the transducer 12 and the further transducer 12a.

It is generally favorable to provide at least two different means for non-optical (acoustical and/or tactile) indications and in particular alarms to the user. In the embodiment of FIG. 1 with a single transducer 12, the pager vibrator 13 is provided for this reason. In the embodiment of FIG. 2, no pager vibrator is necessary because of the further transducer 12a and further noise signal generator 112a. Pager vibrator 13, however, may optionally be present and serve, e.g., as further alarming device and in particular for providing discrete indications and/or user feedback in non-critical situations.

In FIG. 1 and FIG. 2, both the motor 14 and the spindle drive unit 15 are integral part of the ambulatory infusion device. In an alternative configuration, a threaded rod or spindle is integral part of the cartridge 14, while a corresponding drive nut is part of the ambulatory infusion device 1, or vice versa.

In a further configuration, the ambulatory infusion device 1 is not designed as classical syringe driver device where the drug is metered and administered directly out of the cartridge 21. Instead, a down-stream dosing architecture may be foreseen where a primary reservoir (e.g., cartridge 21 or a bag, pouch, or the like) is fluidic coupled with an intermediate dosing cylinder out of which the drug is metered and administered. In this case, the motor 14 is in an operational state operatively coupled with the dosing unit to form a small syringe driver. A valve unit is provided and typically realised integral with the dosing cylinder for alternatively fluidic coupling of the dosing cylinder with the primary reservoir or the infusion tubing 22. The valve unit may also be switched or actuated via the motor 14 or the ambulatory infusion device may have a dedicated valve switching drive that operatively couples with the valve unit. Suited dosing unit designs and architectures are disclosed, e.g., in EP 2 163 273 A1, EP 2 881 128 A1. If a separate drive is foreseen for switching the valve, its operational noise may be tested in the same way as explained before in context of FIG. 1. Further, the transducer 12 and/or the further transducer 12a may receive a valve switching noise that is associated with the valve switching and the valve switching noise may be evaluated by the evaluation unit 113 to determining whether the valve switching noise corresponds to an expected valve switching noise.

Independent from the specific design and architecture, the ambulatory infusion device 1 is generally realized as volumetric metering pump respectively positive displacement pump that is designed for administering well-defined drug volumes in a controlled way substantially independent from the pressure conditions.

The ambulatory infusion device 1 may be configured to be carried, e.g., in a trousers' pocket, with a belt clip or the like, i.e., not directly attached to the body. Alternatively or additionally, the ambulatory infusion device 1 may be designed for direct attachment to the wearer's body e.g., via an adhesive tape, with the infusion cannula 23 projecting from the housing 10.

During regular operation and when the transducer 12 and/or the further transducer 12a may be operatively coupled to the evaluation unit 113 and the evaluation unit 113 may be configured to detect the occurrence of a mechanical shock that occurs, e.g., if the ambulatory infusion device 1 is dropped, resulting in potential damage. If a mechanical shock is detected, (self) testing routines may automatically be initiated and/or a warning or alert may be generated.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. An ambulatory infusion device, comprising:
   a) an electroacoustic transducer; and
   b) a controller configured to operate the electroacoustic transducer as a noise emitter, and alternatively, as a noise receiver, and to determine from a drive noise generated by a motor and received by the electroacoustic transducer a state of the ambulatory infusion device, the controller further configured to:
      i) evaluate operation time of one or more drives of the device using the drive noise received during drug administration and comparing the operation time with an expected operation time,
      ii) detect an unexpected interruption in the drive noise,
      iii) detect an increased overall noise level of the drive noise, and/or
      iv) evaluate the drive noise to determine rotation direction of the drive;
   wherein the transducer comprises hardware that operates as both the receiver and the emitter.

2. The ambulatory infusion device according to claim 1, further comprising a second electroacoustic transducer that is distinct from the electroacoustic transducer, wherein the controller is configured to operate the second electroacoustic transducer as a second noise emitter.

3. The ambulatory infusion device according to claim 2, wherein the controller is configured, while operating the second electroacoustic transducer as the second noise emitter, to simultaneously operate the electroacoustic transducer as the noise receiver.

4. The ambulatory infusion device according to claim 2, wherein the controller is configured operate the second electroacoustic transducer as a second noise receiver and to determine from a second noise that is received by the second electroacoustic transducer a second state of the ambulatory infusion device.

5. The ambulatory infusion device of claim 4, wherein the controller is further configured, while operating the second electroacoustic transducer as the second noise receiver, to simultaneously operate the electroacoustic transducer as the noise emitter to emit an emitted noise, wherein determining the second state of the ambulatory infusion device includes determining whether the second received noise corresponds to noise emitted by the electroacoustic transducer.

6. The ambulatory infusion device according to claim 2, wherein the controller is configured to simultaneously operate both the electroacoustic transducer and the second electroacoustic transducer as the first and the second noise emitters.

7. The ambulatory infusion device according to claim 1, wherein the controller is configured to control a drug administration, the ambulatory infusion device thereby emitting the drive noise.

8. The ambulatory infusion device according to claim 7, wherein evaluating the drive noise includes determining whether the drive noise corresponds to an expected drive noise.

9. The ambulatory infusion device according to claim 7, wherein evaluating the drive noise includes determining whether the drive noise is indicative of fluidic blockage of an infusion path.

10. The ambulatory infusion device according to claim 7, wherein evaluating the drive noise includes determining whether the drive noise is indicative of a defect.

11. The ambulatory infusion device according to claim 7, wherein the drive comprises an electric drive, wherein the drive noise is emitted by the electric drive.

12. The ambulatory infusion device according to claim 1, further comprising the controller having a noise generator module, an evaluation module and a switching module.

13. The ambulatory infusion device according to claim 12, wherein to operate the electroacoustic transducer as a noise emitter, the switching module operatively connects the electroacoustic transducer with the noise generator module.

14. The ambulatory infusion device according to claim 12, wherein, to operate the electroacoustic transducer as a noise receiver, the switching module operatively connects the electroacoustic transducer with the evaluation module.

15. The ambulatory infusion device according to claim 1, wherein transmitter and receiver hardware are located in the same housing.

16. The ambulatory infusion device according to claim 1, wherein the controller is configured to perform at least two of the functions (i)-(iv) of step b).

17. The ambulatory infusion device according to claim 16, wherein the controller is configured to perform all of the functions (i)-(iv) of step b).

18. A method for operating an electroacoustic transducer that is part of an ambulatory infusion device, the method including:
a) operating the electroacoustic transducer as a noise emitter to emit an emitted noise; and
b) operating the electroacoustic transducer as a noise receiver and determining a functional state of the ambulatory infusion device from a drive noise generated by a motor and received by the electroacoustic transducer;
c) using a controller to:
i) evaluate operation time of one or more drives of the device using the drive noise received during drug administration and comparing the operation time with an expected operation time,
ii) detect an unexpected interruption in the drive noise,
iii) detect an increased overall noise level of the drive noise, and/or
iv) evaluate the drive noise to determine rotational direction of the drive;
wherein the transducer comprises hardware that operates as both the receiver and the emitter.

19. The method according to claim 18, further comprising operating a second electroacoustic transducer, distinct from the electroacoustic transducer, as a noise emitter and simultaneously operating the electroacoustic transducer as a noise receiver.

20. The method according to claim 19, further comprising simultaneously operating both the electroacoustic transducer and the second electroacoustic transducer as acoustic noise emitters.

21. The method according to claim 18, wherein the controller is used to perform at least two of the functions (i)-(iv) of step c).

22. The method according to claim 21, wherein the controller is used to perform all of the functions (i)-(iv) of step c).

23. An extracorporeal ambulatory infusion device, comprising:
a) a control unit, wherein the control unit includes a noise generator module, an evaluation module and a switching module;
b) an electroacoustic transducer;
wherein the control unit is configured to:
operate the electroacoustic transducer as a noise emitter, wherein the switching module operatively connects the electroacoustic transducer with the noise generator module; and
operate the electroacoustic transducer alternatively as a noise receiver, wherein the switching module operatively connects the electroacoustic transducer with the evaluation module, wherein the evaluation module is configured to determine from a drive noise from a motor and received by the electroacoustic transducer a state of the ambulatory infusion device.

24. The ambulatory infusion device according to claim 23, wherein the transducer comprises hardware that operates as both the receiver and the emitter.

25. The ambulatory infusion device according to claim 24, wherein the transducer hardware for the receiver and emitter is located in a single housing.

* * * * *